United States Patent
Kim

(10) Patent No.: US 10,271,908 B2
(45) Date of Patent: Apr. 30, 2019

(54) OPTICAL TRACKING SYSTEM AND TRACKING METHOD FOR OPTICAL TRACKING SYSTEM

(71) Applicant: KOH YOUNG TECHNOLOGY INC., Seoul (KR)

(72) Inventor: Sang Yong Kim, Seoul (KR)

(73) Assignee: KOH YOUNG TECHNOLOGY INC., Seoul (KR)

(*) Notice: Subject to any disclaimer, the term of this patent is extended or adjusted under 35 U.S.C. 154(b) by 0 days.

(21) Appl. No.: 15/537,582

(22) PCT Filed: Dec. 18, 2015

(86) PCT No.: PCT/KR2015/013967
§ 371 (c)(1),
(2) Date: Jun. 19, 2017

(87) PCT Pub. No.: WO2016/099212
PCT Pub. Date: Jun. 23, 2016

(65) Prior Publication Data
US 2018/0263708 A1 Sep. 20, 2018

(30) Foreign Application Priority Data
Dec. 19, 2014 (KR) .................... 10-2014-0183829

(51) Int. Cl.
*A61B 34/20* (2016.01)
*A61B 34/00* (2016.01)
(Continued)

(52) U.S. Cl.
CPC .............. *A61B 34/20* (2016.02); *A61B 34/00* (2016.02); *A61B 90/36* (2016.02); *A61B 90/39* (2016.02);
(Continued)

(58) Field of Classification Search
CPC ......... A61B 34/20; A61B 90/36; A61B 90/39; A61B 2034/2055; A61B 2090/3983;
(Continued)

(56) References Cited

U.S. PATENT DOCUMENTS

2002/0065461 A1   5/2002   Cosman
2005/0182319 A1*  8/2005   Glossop ................ A61B 5/061
                                                                    600/424
(Continued)

FOREIGN PATENT DOCUMENTS

EP    2 329 786      *  6/2011
JP    2008-2867          1/2008
(Continued)

OTHER PUBLICATIONS

International Search Report for International Application No. PCT/KR2015/013967, dated Apr. 5, 2016.
(Continued)

*Primary Examiner* — Qian Yang
(74) *Attorney, Agent, or Firm* — Kile Park Reed & Houtteman PLLC

(57) ABSTRACT

An optical tracking system includes a reference marker part stationarily disposed relative to a first region; a sticker marker part attached in a sticker form to a second region capable of being rigidly registered with the first region; a shape measurement part measuring three-dimensional shapes of the first region and the second region; a tracking sensor part sensing the reference marker part and the shape measurement part; and a processing part acquiring a first coordinate transformation relationship among the reference marker part, the tracking sensor part, the shape measurement part, and the first region of the patent and a second coordinate transformation relationship among the reference marker part, the tracking sensor part, the shape measurement part,
(Continued)

and the second region of the patient and tracking the first region by extracting a third coordinate transformation relationship between the first region and the second region.

18 Claims, 6 Drawing Sheets

(51) Int. Cl.
    *A61B 90/00*     (2016.01)
    *G06T 7/50*     (2017.01)
    *G06T 7/11*     (2017.01)
    *G06T 3/00*     (2006.01)

(52) U.S. Cl.
    CPC .............. *G06T 3/0068* (2013.01); *G06T 7/11* (2017.01); *G06T 7/50* (2017.01); *A61B 2034/2055* (2016.02); *A61B 2034/2065* (2016.02); *A61B 2090/363* (2016.02); *A61B 2090/364* (2016.02); *A61B 2090/373* (2016.02); *A61B 2090/3735* (2016.02); *A61B 2090/3937* (2016.02); *A61B 2090/3983* (2016.02); *G06T 2207/30096* (2013.01)

(58) Field of Classification Search
    CPC ... A61B 2090/364; G06T 7/50; G06T 3/0068; G06T 7/11; G06T 2207/30096
    See application file for complete search history.

(56) References Cited

U.S. PATENT DOCUMENTS

| | | | |
|---|---|---|---|
| 2007/0238986 A1* | 10/2007 | Graumann | A61B 6/12 600/424 |
| 2008/0013809 A1 | 1/2008 | Zhu et al. | |
| 2011/0098553 A1* | 4/2011 | Robbins | A61B 5/055 600/410 |
| 2011/0105895 A1* | 5/2011 | Kornblau | A61B 34/20 600/426 |
| 2011/0270084 A1 | 11/2011 | Choi et al. | |
| 2012/0082342 A1 | 4/2012 | Kim et al. | |
| 2013/0060146 A1 | 3/2013 | Yang et al. | |
| 2013/0108979 A1 | 5/2013 | Daon | |
| 2013/0131504 A1 | 5/2013 | Daon | |
| 2014/0228675 A1 | 8/2014 | Daon | |
| 2015/0049907 A1 | 2/2015 | Hong et al. | |
| 2015/0287236 A1 | 10/2015 | Winne et al. | |
| 2016/0000518 A1* | 1/2016 | Thoranaghatte | A61B 19/5244 703/11 |

FOREIGN PATENT DOCUMENTS

| | | |
|---|---|---|
| JP | 4265698 | 2/2009 |
| JP | 2011-182983 | 9/2011 |
| KR | 10-0961661 | 6/2010 |
| KR | 10-1049507 | 7/2011 |
| KR | 10-2012-0035021 | 4/2012 |
| KR | 10-2013-0121753 | 11/2013 |
| KR | 10-2014-0088167 | 7/2014 |
| WO | 98/35720 | 8/1998 |
| WO | 2013/162332 | 10/2013 |
| WO | 2014068106 | 5/2014 |

OTHER PUBLICATIONS

Chinese Office Action with English translation for Chinese Application Serial No. 2018120701498240, dated Dec. 12, 2018.

* cited by examiner

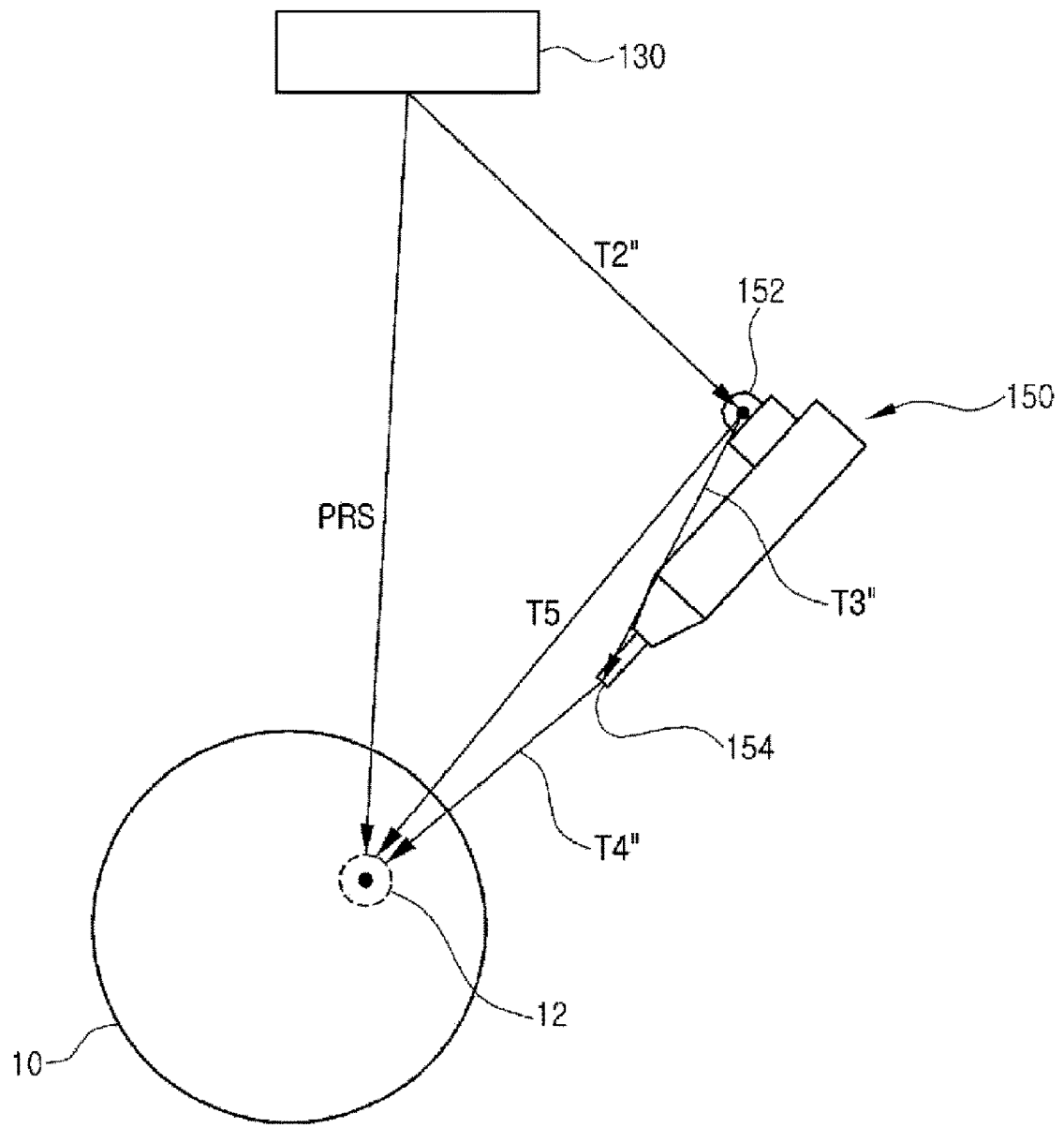

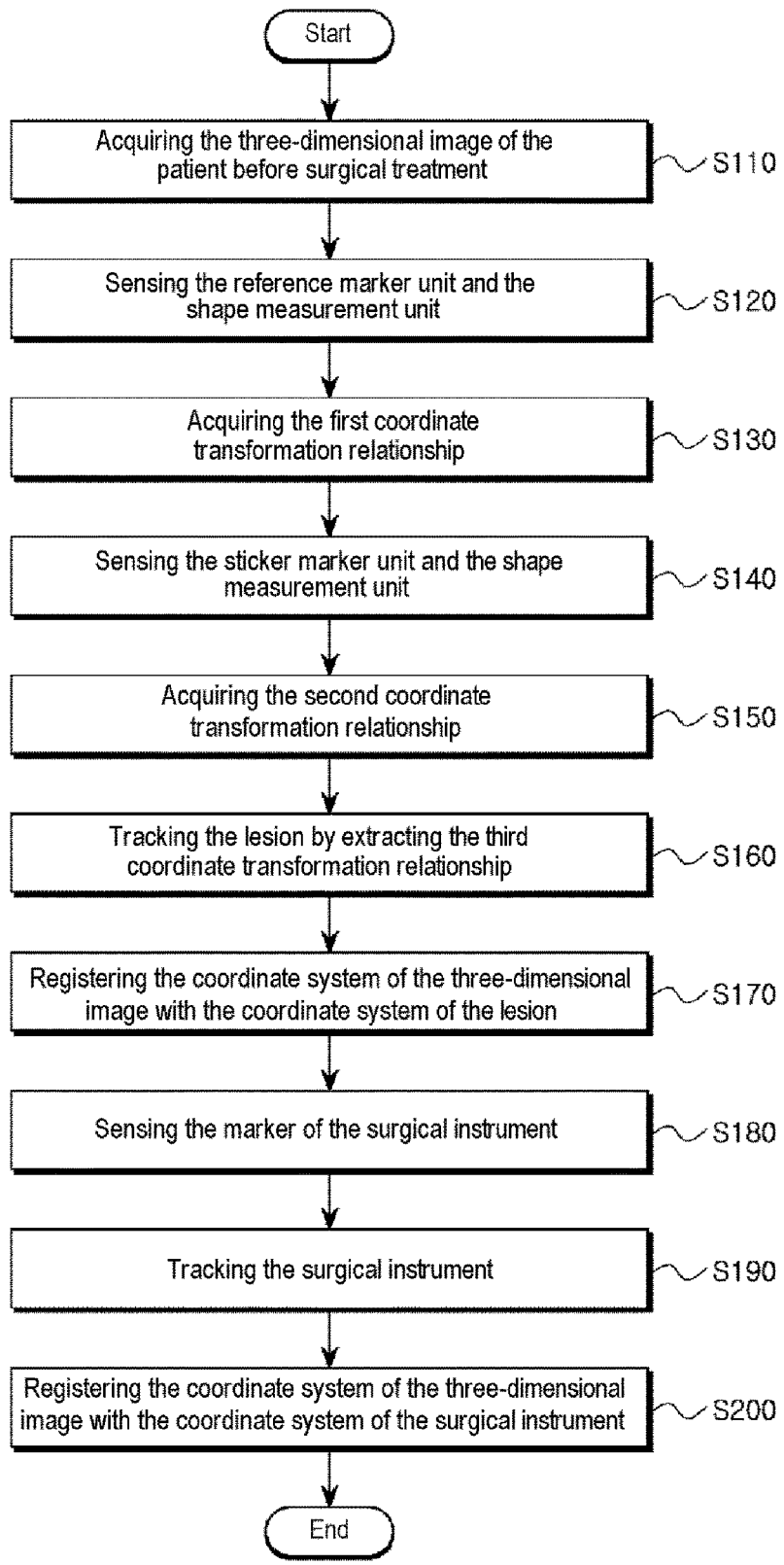

OPTICAL TRACKING SYSTEM AND TRACKING METHOD FOR OPTICAL TRACKING SYSTEM

TECHNICAL FIELD

The present disclosure relates to an optical tracking system and a tracking method for an optical tracking system and, more particularly, to an optical tracking system for tracking a patient or a surgical instrument and a tracking method for an optical tracking system.

BACKGROUND ART

Recently, in a surgery for treating a lesion of a patient, an image-guided surgery using a pre-captured image is widely utilized. In particular, when a surgery is to be performed, high accuracy in performing the surgery without jeopardizing important nerves and major organs in a body of a patient is required based on the images captured in advance.

In general, images captured in advance include three-dimensional images obtained by MRI imaging, CT imaging, or the like. At the start of a surgery, it is necessary to perform registration to match a coordinate system of the three-dimensional images captured in advance with a coordinate system of a patient. While the surgery is in progress, it is necessary to determine in real time a change in position and posture according to a movement of the patient and a surgical instrument. In addition, when the posture of the patient is changed during the surgery, there is a need to perform re-registration to re-match a coordinate system of the patient with the three-dimensional images captured in advance to continuously track the patient or a lesion.

In the related art, a dynamic reference base (DRB) has been used for such registration and tracking. That is, after the DRB is attached to a patient, a three-dimensional image such as CT or the like is captured. Then, at the start of a surgery, registration is performed to match a coordinate system of the three-dimensional image with a coordinate system of the patient. While the surgery is in progress, a surgical instrument is tracked based on the DRB, thereby tracking the position or the like of the surgical instrument relative to a lesion of the patient. In this case, for the purpose of registration, it is necessary to capture a three-dimensional image in advance while keeping the DRB attached to the patient. For accurate tracking, it is necessary to firmly attach the DRB to the patient.

To this end, in the related art, several methods have been adopted such as a method for sensing and tracking a marker after implanting the marker in a bone of a patient, a method for sensing and tracking a template to which a marker is attached by having a patient bite the template with his or her teeth, and a method using a STAMP (Surface Template-Assisted Marker Position) processed by generating an artificial structure.

However, the above conventional methods suffer from a variety of problems such as the difficulty involved in attaching the marker, side effects caused by implanting the marker in the bone, a reduction in accuracy and reliability attributable to the change in the marker position which may be generated when the marker is bitten by teeth, inconvenience in manufacturing an expensive STAMP before a surgery and the substantial time and cost required for manufacturing the STAMP, etc. Moreover, in the case of the conventional methods, even when the DRB is firmly attached to a patient, if the patient moves, the distance between the DRB and the lesion of the patient or the posture of the patient may change. Thus, accurate tracking cannot be carried out and re-registration cannot accurately be performed, thereby resulting in a problem that the DRB cannot be used. Accordingly, in the case of the conventional methods, a surgery is performed under the assumption that the patient does not move. In practice, however, it is often the case that a patient moves during a surgery. Thus, it is difficult to carry out the tracking in a substantially accurate manner.

Accordingly, there is a need to develop a registration method capable of acquiring an accurate registration result in a shorter time and with a reduced cost. Further, there is a need to develop a tracking system and tracking method in which tracking is performed in a relatively accurate and easy manner even if a patient moves or the posture of the patent changes during a surgery.

SUMMARY

Accordingly, it is an objective of the present disclosure to provide an optical tracking system capable of accurately and easily tracking a patient or a surgical instrument in a shorter time and with a reduced cost and capable of enhancing the convenience of a patient and an operator.

Another objective of the present disclosure is to provide a tracking method for an optical tracking system capable of accurately and easily tracking a patient or a surgical instrument in a shorter time and with a reduced cost and capable of enhancing the convenience of a patient and an operator.

According to one exemplary embodiment of the present disclosure, an optical tracking system is provided for tracking a patient or a surgical instrument for surgically treating the patient by using a three-dimensional image acquired in advance before surgically treating the patient and including a first region corresponding to a lesion of the patient. The optical tracking system includes a reference marker part, a sticker marker part, a shape measurement part, a tracking sensor part, and a processing part. The reference marker part is stationarily disposed in relative to the first region of the patient. The sticker marker part is attached in a sticker form to a second region capable of being rigidly registered with the first region. The shape measurement part is configured to measure three-dimensional shapes of the first region and the second region. The tracking sensor part is configured to sense the reference marker part and the shape measurement part so as to track the reference marker part and the shape measurement part, respectively. The processing part is configured to acquire a first coordinate transformation relationship among the reference marker part, the tracking sensor part, the shape measurement part, and the first region of the patent and a second coordinate transformation relationship among the reference marker part, the tracking sensor part, the shape measurement part, and the second region of the patient based on a sensing result of the tracking sensor part and a measurement result of the shape measurement part and to track the first region relative to the tracking sensor part by extracting a third coordinate transformation relationship between the first region and the second region from the first and second coordinate transformation relationships.

In one embodiment, when the shape measurement part is disposed in a first position, the processing part may be configured to acquire the first coordinate transformation relationship by acquiring a coordinate transformation relationship between the reference marker part and the tracking sensor part and a coordinate transformation relationship between the shape measurement part and the tracking sensor part based on a sensing result of the tracking sensor part and by acquiring a coordinate transformation relationship between the first region of the patient and the shape measurement part based on a measurement result of the shape measurement part disposed in the first position. Furthermore, when the shape measurement part is disposed in a second position differing from the first position, the processing part may be configured to acquire the second coordinate transformation relationship by acquiring a coordinate transformation relationship between the reference marker part and the tracking sensor part and a coordinate transformation relationship between the shape measurement part and the tracking sensor part based on a sensing result of the tracking sensor part and by acquiring a coordinate transformation relationship between the second region of the patient and the shape measurement part based on a measurement result of the shape measurement part disposed in the second position.

For example, the shape measurement part may include a measurement device configured to measure a three-dimensional shape and a marker installed on the measurement device, the tracking sensor part may be configured to sense the marker of the shape measurement part, and the processing part may be configured to acquire a coordinate transformation relationship between the marker of the shape measurement part and the tracking sensor part and a coordinate transformation relationship between the measurement device of the shape measurement part and the marker of the shape measurement part.

For example, the coordinate transformation relationships may be expressed as coordinate transformation matrices, and the processing part may be configured to define the first coordinate transformation relationship and the second coordinate transformation relationship according to the following mathematical formula:

$$PR = T1^{-1} T2 T3 T4$$

where PR is a coordinate transformation matrix of the first region or the second region of the patient with respect to the reference marker part, T1 is a coordinate transformation matrix of the reference marker part with respect to the tracking sensor part, T2 is a coordinate transformation matrix of the marker of the shape measurement part with respect to the tracking sensor part, T3 is a coordinate transformation matrix of the measurement device of the shape measurement part with respect to the marker of the shape measurement part, and T4 is a coordinate transformation matrix of the first region or the second region of the patient with respect to the measurement device of the shape measurement part.

In one embodiment, the tracking sensor part may be configured to measure information for acquiring the coordinate transformation matrix T1 of the reference marker part with respect to the tracking sensor part and the coordinate transformation matrix T2 of the marker of the shape measurement part with respect to the tracking sensor part, the shape measurement part may be configured to measure information for acquiring the coordinate transformation matrix T4 of the first region or the second region of the patient with respect to the measurement device of the shape measurement part, and the processing part may be configured to acquire the coordinate transformation matrices T1, T2, and T4 by using the measured information and to calculate, from the acquired coordinate transformation matrices T1, T2, and T4, the coordinate transformation matrix T3 of the measurement device of the shape measurement part with respect to the marker of the shape measurement part and the coordinate transformation matrix PR of the first region or the second region of the patient with respect to the reference marker part.

For example, the measurements of the tracking sensor part and the shape measurement part may be performed two or more times with respect to each of the first region and the second region of the patient.

The third coordinate transformation relationship may be expressed as a coordinate transformation matrix PRX defined by the following mathematical formula:

$$PRX = PR2^{-1} PR1$$

where PR1 is a coordinate transformation matrix of the first region of the patient with respect to the reference marker part, and PR2 is a coordinate transformation matrix of the second region of the patient with respect to the reference marker part.

At this time, the processing part may be configured to relatively track the first region with respect to the tracking sensor part by using the coordinate transformation matrix PRX.

The processing part may be configured to register a coordinate system of the three-dimensional image acquired in advance before surgically treating the patient with a coordinate system of the first region of the patient based on the three-dimensional shapes measured in the shape measurement part. Furthermore, the processing part may be configured to re-register the coordinate system of the three-dimensional image acquired in advance before surgically treating the patient with the coordinate system of the first region of the patient based on the three-dimensional shape of the second region of the patient measured in the shape measurement part and the third coordinate transformation relationship.

The optical tracking system may further include a surgical instrument provided to surgically treat the patient and including a marker. The tracking sensor part may be configured to sense the marker of the surgical instrument so as to track the surgical instrument. The processing part may be configured to relatively track the surgical instrument with respect to the first region of the patient by using a tracking result of the surgical instrument tracked by the tracking sensor part and a tracking result of the first region of the patient relatively tracked with respect to the tracking sensor part.

For example, the sticker marker part may include a marker having a three-dimensional shape. A plurality of sticker marker parts may be respectively attached to different regions.

The processing part may register a coordinate system of the three-dimensional image acquired in advance before surgically treating the patient with a coordinate system of the surgical instrument relatively defined with respect to the patient, based on a registration result of the coordinate system of the three-dimensional image and the coordinate system of the patient.

According to another exemplary embodiment of the present disclosure, a tracking method for an optical tracking system includes: acquiring a three-dimensional image including a first region corresponding to a lesion of a patient before surgically treating the patient; sensing, by a tracking sensor part, a shape measurement part disposed in a first position so as to measure a three-dimensional shape of a reference marker part disposed away from the first region of the patient and a three-dimensional shape of the first region; acquiring a first coordinate transformation relationship among the reference marker part, the tracking sensor part, the shape measurement part, and the first region of the patient based on a first sensing result of the tracking sensor part and a measurement result of the shape measurement part disposed in the first position; sensing, by the tracking sensor part, the shape measurement part disposed in a second position so as to measure a three-dimensional shape of a sticker marker part attached in a sticker form to a second region capable of being rigidly registered with the first region and a three-dimensional shape of the second region; acquiring a second coordinate transformation relationship among the reference marker part, the tracking sensor part, the shape measurement part, and the second region of the patient based on a second sensing result of the tracking sensor part and a measurement result of the shape measurement part disposed in the second position; and tracking the first region relative to the tracking sensor part by extracting a third coordinate transformation relationship between the first region and the second region from the first and second coordinate transformation relationships.

In one embodiment, the acquiring the first coordinate transformation relationship may include acquiring the first coordinate transformation relationship by acquiring a coordinate transformation relationship between the reference marker part and the tracking sensor part and a coordinate transformation relationship between the shape measurement part and the tracking sensor part based on the first sensing result of the tracking sensor part and by acquiring a coordinate transformation relationship between the first region of the patient and the shape measurement part based on the measurement result of the shape measurement part disposed in the first position. Furthermore, the acquiring the second coordinate transformation relationship may include acquiring the second coordinate transformation relationship by acquiring a coordinate transformation relationship between the reference marker part and the tracking sensor part and a coordinate transformation relationship between the shape measurement part and the tracking sensor part based on the second sensing result of the tracking sensor part and by acquiring a coordinate transformation relationship between the second region of the patient and the shape measurement part based on a measurement result of the shape measurement part disposed in the second position.

For example, the tracking method may further include registering a coordinate system of the three-dimensional image acquired in advance before surgically treating the patient with a coordinate system of the first region of the patient based on the three-dimensional shapes measured in the shape measurement part.

The tracking method may further include: sensing a marker of a surgical instrument so as to track the surgical instrument for surgically treating the patient; and relatively tracking the surgical instrument with respect to the first region of the patient by using a tracking result of the surgical instrument tracked by the tracking sensor part and a tracking result of the first region of the patient relatively tracked with respect to the tracking sensor part.

The tracking method may further include after the relatively tracking the surgical instrument with respect to the first region of the patient, registering a coordinate system of the three-dimensional image with a coordinate system of the surgical instrument relatively defined with respect to the first region of the patient according to the tracking of the surgical instrument, based on a registration result of the coordinate system of the three-dimensional image and the coordinate system of the first region of the patient.

According to a further exemplary embodiment of the present disclosure, an optical tracking system is provided for tracking a patient or a surgical instrument for surgically treating the patient by using a three-dimensional image acquired in advance before surgically treating the patient and including a first region corresponding to a lesion of the patient. The optical tracking system includes a sticker marker part, a shape measurement part, a tracking sensor part and a processing part. The sticker marker part is attached in a sticker form to a second region capable of being rigidly registered with the first region. The shape measurement part is configured to measure three-dimensional shapes of the first region and the second region. The tracking sensor part is configured to sense the sticker marker part and the shape measurement part so as to track the sticker marker part and the shape measurement part, respectively. The processing part is configured to acquire a coordinate transformation relationship between the sticker marker part and the tracking sensor part and a coordinate transformation relationship between the shape measurement part and the tracking sensor part based on a sensing result of the tracking sensor part, to acquire a coordinate transformation relationship between the first region of the patient and the shape measurement part based on a measurement result of the shape measurement part, and to relatively define a coordinate system of the patient with respect to the sticker marker part by using the acquired coordinate transformation relationships.

According to the present disclosure, the optical tracking system includes the sticker marker part provided in a position capable of being rigidly registered with a lesion. The shape measurement part measures three-dimensional shapes of the lesion and the sticker marker part. The tracking sensor part senses the shape measurement part and the reference marker part. The coordinate transformation relationship between the lesion and the sticker marker part is extracted from the coordinate transformation relationships between them. Thus, it is possible to track the position and posture of the lesion with respect to the tracking sensor part by merely performing a work in which the shape measurement part tracks the sticker marker part by using the coordinate transformation relationship.

Furthermore, the process in which the shape measurement part measures the sticker marker part may be re-performed with ease. Therefore, even when the patient moves or the posture changes, it is possible to easily and accurately track the lesion and the surgical instrument in real time during surgical treatment by using the coordinate transformation relationship between the lesion and the sticker marker part.

Furthermore, after surgical treatment is started, the lesion may be tracked when the shape measurement part measures the sticker marker part without having to measure the lesion. Therefore, there is no need to move the shape measurement part during surgical treatment in order to measure the lesion and it is possible to prevent a problem that the shape measurement part becomes an obstacle in surgical treatment when the shape measurement part is positioned around the lesion during the surgical treatment. Moreover, since the attachment position of the sticker marker part can be selected relatively freely, it is possible to dispose the shape measurement part in a position where the shape measurement part does not become an obstacle in surgical treatment. In addition, the sticker marker part is of a sticker attachment type. Thus, the sticker marker part may be formed in a shape that does not become an obstacle in surgical treatment, and may be attached in a position where the sticker marker part does not become an obstacle in surgical treatment. A plurality of sticker marker parts may be adopted and may be utilized in such a way as not to hinder surgical treatment.

Furthermore, when the sticker marker part is manufactured in a three-dimensional shape, it is possible to facilitate registration through the addition of feature points. If the sticker marker part is directly tracked by the tracking sensor part, it is possible to omit the reference marker part. In addition, in the case of adopting two or more sticker marker parts and two or more shape measurement parts corresponding thereto, it is possible to measure an angle by using the coordinate transformation relationship between the sticker marker parts. This makes it possible to perform surgical treatment such as knee surgery or the like through the measurement of an angle.

In addition, registration can be performed by using the three-dimensional shape of the patient measured during surgical treatment as a marker. Therefore, even though a DRB is not directly attached to the patient, the coordinate system of the three-dimensional image acquired in advance before surgical treatment can be registered with the coordinate system of the patient and the coordinate system of the surgical instrument, which may move in real time during surgical treatment. Further, even when acquiring the three-dimensional image in advance, the DRB does not need to be attached and the resetting and re-registration of the coordinate system can be performed at any time.

Accordingly, it is possible to solve the problems inherent in the related art, such as the pain experienced by the patient and an error due to directly attaching a marker to the patient, the onerous work of manufacturing the STAMP before a surgery, the substantial time and the cost required in manufacturing the STAMP, etc.

That is, the setting of the coordinate system of the patient and the registration of the images can be expeditiously performed in an operating room without a separate preparation process. It is therefore possible to accurately and easily perform the setting of the coordinate system of the patient and the coordinate system of the surgical instrument and the registration of the images in a shorter time and with a reduced cost. Further, it is possible to alleviate the pain of the patient and side effects by using the sticker-type sticker marker part instead of the DRB.

Thus, according to the optical tracking system according to the present disclosure and the tracking method using the same, it is possible to greatly enhance the convenience of the patient and the operator.

BRIEF DESCRIPTION OF THE DRAWINGS

FIG. 5 is a conceptual diagram for explaining tracking of a surgical instrument and registration in the optical tracking system shown in FIG. 1.

FIG. 6 is a flowchart showing a coordinate registration method and a tracking method for an optical tracking system according to one embodiment of the present disclosure.

DETAILED DESCRIPTION

Figure 1:
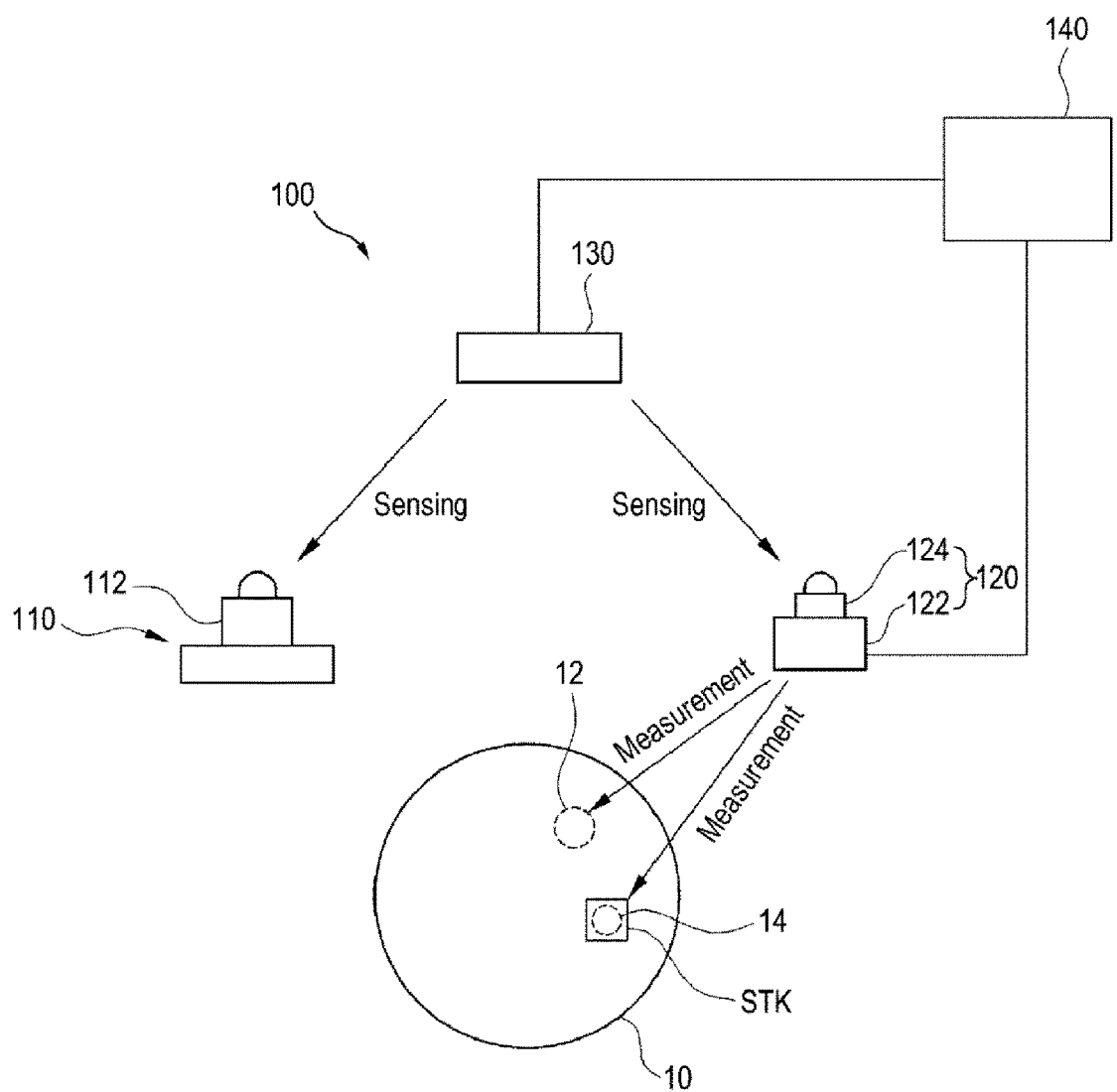
FIG. 1 is a conceptual diagram showing an optical tracking system according to one embodiment of the present disclosure.

The present disclosure may be diversely modified and may have various forms. Specific embodiments will be illustrated in the drawings and will be described in detail. However, this is not intended to limit the present disclosure to specific forms of disclosure. It is to be understood that the present disclosure includes all modifications, equivalents and substitutions which fall within the spirit and technical scope of the present disclosure.

The terms "first" and "second" may be used for describing various components. However, the components shall not be limited by these terms. These terms are used only for the purpose of distinguishing one component from another component. For example, a first component may be named as a second component without departing from the scope of rights of the present disclosure. Similarly, a second component may be named as a first component.

The terms used herein are merely used to describe specific embodiments and are not intended to limit the present disclosure. The singular expression includes plural expressions unless the context clearly indicates otherwise. It should be understood that as used herein, the terms such as "including," "having," and the like are intended to specify the existence of the stated features, numbers, steps, actions, components, parts or combinations thereof and are not intended to preclude in advance the possibility of the existence or addition of one or more other features, numbers, steps, actions, components, parts or combinations thereof.

Unless otherwise defined, all terms used herein, including technical or scientific terms, have the same meanings as generally understood by those having ordinary skill in the art to which the present disclosure belongs.

Commonly used terms such as terms defined in a dictionary or the like are to be interpreted as the meanings consistent with the contextual meanings of the related art. Unless clearly defined herein, such terms are not interpreted in an ideal or overly formal sense.

Preferred embodiments of the present disclosure will now be described in more detail with reference to the accompanying drawings.

FIG. 1 is a conceptual diagram showing an optical tracking system according to one embodiment of the present disclosure.

Referring to FIG. 1, the optical tracking system according to one embodiment of the present disclosure is provided to track a patient 10 or a surgical instrument for surgically treating the patient 10, using a three-dimensional image, which is acquired in advance before surgically treating the patient 10 and includes a first region 12 corresponding to a lesion of the patient 10.

The three-dimensional image is an image acquired in advance before surgically treating the patient 10 and may be utilized as a reference image at the time of surgically treating the patient 10. The term "surgical treatment" or "surgically treating" used herein includes any medical treatment for a patient, including a surgery. For example, the three-dimensional image may include a CT (Computed Tomography) image generally acquired in a hospital for diagnosis and treatment. Alternatively, the three-dimensional image may include other three-dimensional images such as an MRI (Magnetic Resonance Imaging), etc. Further, the three-dimensional image referred to herein is a concept that includes an image obtained by manipulating or reconstructing a directly captured image such as a CT image or the like, and includes both a multi-plane reconstruction image and a three-dimensional reconstruction image that are widely used for actual surgical treatment.

The optical tracking system 100 includes a reference marker part 110, a shape measurement part 120, a tracking sensor part 130, a processing part 140, and a sticker marker part STK. The optical tracking system 100 is provided to track the patient 10 or the surgical instrument for surgically treating the patient 10, using a three-dimensional image acquired in advance before surgically treating the patient 10 and including a first region 12 corresponding to a lesion of the patient 10.

The reference marker part 110 is stationarily disposed relative to the first region 12 of the patient 10. The first region 12 is a region corresponding to a lesion of the patient 10 and is a region to be surgically treated.

A marker 112 is installed on the reference marker part 110. The marker 112 is capable of radiating energy or a signal so that the energy or the signal can be sensed by the tracking sensor part 130 discussed below. For example, a plurality of markers may be installed on the reference marker part 110. A single marker having a predetermined pattern may also be installed on the reference marker part 110.

The reference marker part 110 corresponds to a conventional DRB. However, the reference marker part 110 does not serve as a registration reference like the conventional DRB. Therefore, it is not necessary to attach the reference marker part 110 to the patient 10 when capturing a three-dimensional image such as CT, MRI, or the like. Further, the conventional DRB has to be directly attached to the patient 10 and has to be firmly attached to the patient 10. In contrast, the reference marker part 110 may not only be directly attached to the patient 10, but also be merely fixed relative to the patient 10. Thus, the reference marker part 110 may be attached to a stationary object such as a bed in an operating room or the like and it is not necessary to strictly fix the reference marker part 110 to the patient 10.

The sticker marker part STK is attached in a sticker form to a second region 14 capable of being rigidly registered with the first region 12. The second region 14 may be defined in any position as long as the second region 14 is capable of being rigidly registered with the first region 12. The term "rigid body registration" or the expression "being rigidly registered" does not mean rigid body registration or being rigidly registered in a strict sense and may be flexibly construed depending on the precision and accuracy of surgical treatment for the patient 10.

For example, the sticker marker part STK may include a marker having a three-dimensional shape. A plurality of sticker marker parts STK may be respectively attached to different regions.

The shape measurement part 120 measures three-dimensional shapes of the first region 12 and the second region 14.

As one example, the shape measurement part 120 may include a measurement device 122 and a marker 124.

The measurement device 122 measures a three-dimensional shape with respect to the first region 12 of the patient 10 included in the three-dimensional image and measures a three-dimensional shape with respect to the second region 14 of the patient 10 existing in a position capable of being rigidly registered with the first region 12. At this time, the shape measurement part 120 may be disposed in a first position in a corresponding relationship with the first region 12 and may be disposed in a second position in a corresponding relationship with the second region 14. Since the first position and the second position are disposed in a corresponding relationship with the first region 12 and the second region 14, respectively, it may be preferred that the first position and the second position are different positions. However, the first position and the second position may be the same position.

In one embodiment, the measurement device 122 may irradiate a grid-patterned light on the first region 12 or the second region 14 of the patient 10, acquire a reflective image for the first region 12 or the second region 14 of the patient 10 according to the grid-patterned light, and measure a three-dimensional shape by applying a bucket algorithm to the acquired reflective image. In addition, the measurement device 122 may acquire a three-dimensional image from the measured three-dimensional shape.

In another embodiment, the measurement device 122 may include an optical coherence tomography (OCT) device. The OCT device is a high-resolution image diagnostic device capable of converting a microstructure inside a living tissue into a three-dimensional image by combining a light interference phenomenon and a principle of a confocal microscope and may be, for example, an OCT device configured to convert a cross section of a living tissue to an image in a non-contact and non-invasive manner using a light source of a region of near infrared rays (having a wavelength of 0.6 μm to 1.3 μm). Specifically, for example, the OCT device may operate based on a Michelson interferometer. That is, when the optical signal generated from the light source is split into two optical signals in an optical coupler and is incident on a reference stage and a sample stage, the reference light returned from the reference stage and the sample light scattered rearward in the sample stage meet again and cause light interference. The cross section of an object to be imaged may be converted to an image by using such a light interference signal.

The marker 124 is installed on the measurement device 122. The marker 124 may radiate energy or a signal so that the energy or the signal can be sensed by the tracking sensor part 130 which will be described below. For example, a plurality of markers may be installed on the shape measurement part 120. A single marker having a predetermined pattern may also be installed on the shape measurement part 120.

The tracking sensor part 130 is configured to sense the reference marker part 110 and the shape measurement part 120 so as to track each of the reference marker part 110 and the shape measurement part 120.

For example, the tracking sensor part 130 may sense the marker 112 of the reference marker part 110 and may sense the marker 124 of the shape measurement part 120. Accordingly, the position and/or the posture of the reference marker part 110 may be determined and the position and/or the posture of the shape measurement part 120 may be determined.

The processing part 140 may include, for example, a computer or a central processing part of a computer.

The processing part 140 acquires a first coordinate transformation relationship among the reference marker part 110, the tracking sensor part 130, the shape measurement part 120, and the first region 12 of the patient 10 and a second coordinate transformation relationship among the reference marker part 110, the tracking sensor part 130, the shape measurement part 120, and the second region 14 of the patient 10, based on the sensing result of the tracking sensor part 130 and the measurement result of the shape measurement part 120. The processing part 140 extracts a third coordinate transformation relationship between the first region 12 and the second region 14 from the first and second coordinate transformation relationships and tracks the first region 12 relative to the tracking sensor part 130.

Specifically, when the shape measurement part 120 is disposed in the first position, the processing part 140 acquires a coordinate transformation relationship between the reference marker part 110 and the tracking sensor part 130 and a coordinate transformation relationship between the shape measurement part 120 and the tracking sensor part 130, based on the sensing result of the tracking sensor part 130. As a result, the processing part 140 acquires a coordinate transformation relationship between the first region 12 of the patient 10 and the shape measurement part 120, based on the measurement result of the shape measurement part 120. The first coordinate transformation relationship may be acquired from the coordinate transformation relationships acquired as above. Herein, the coordinate transformation relationships may be defined, for example, in the form of matrices.

Further, when the shape measurement part 120 is disposed in the second position, the processing part 140 acquires a coordinate transformation relationship between the reference marker part 110 and the tracking sensor part 130 and a coordinate transformation relationship between the shape measurement part 120 and the tracking sensor part 130, based on the sensing result of the tracking sensor part 130. As a result, the processing part 140 acquires a coordinate transformation relationship between the second region 14 of the patient 10 and the shape measurement part 120 based on the measurement result of the shape measurement part 120. The second coordinate transformation relationship may be acquired from the coordinate transformation relationships acquired as above. Herein, the coordinate transformation relationships may be defined, for example, in the form of matrices.

The processing part 140 extracts a third coordinate transformation relationship between the first region 12 and the second region 14 from the first and second coordinate transformation relationships acquired as above and tracks the first region 12 relative to the tracking sensor part 130.

Meanwhile, there is a small difference between the measurement position of the measurement device 122 of the shape measurement part 120 and the position of the marker 124 of the shape measurement part 120. Therefore, the error attributable to the positional difference between the measurement device 122 and the marker 124 may be calibrated in order to accurately define the coordinate system. Accordingly, the processing part 140 may individually acquire the coordinate transformation relationship between the marker 124 of the shape measurement part 120 and the tracking sensor part 130 and the coordinate transformation relationship between the measurement device 122 of the shape measurement part 120 and the marker 124. For example, the coordinate transformation relationships may be expressed as coordinate transformation matrices.

Hereinafter, the solving process and modeling setting of the optical tracking system 100 for tracking the first region 12 of the patient 10 by using the coordinate transformation relationships will be described in more detail with reference to the drawings.

Figure 2:
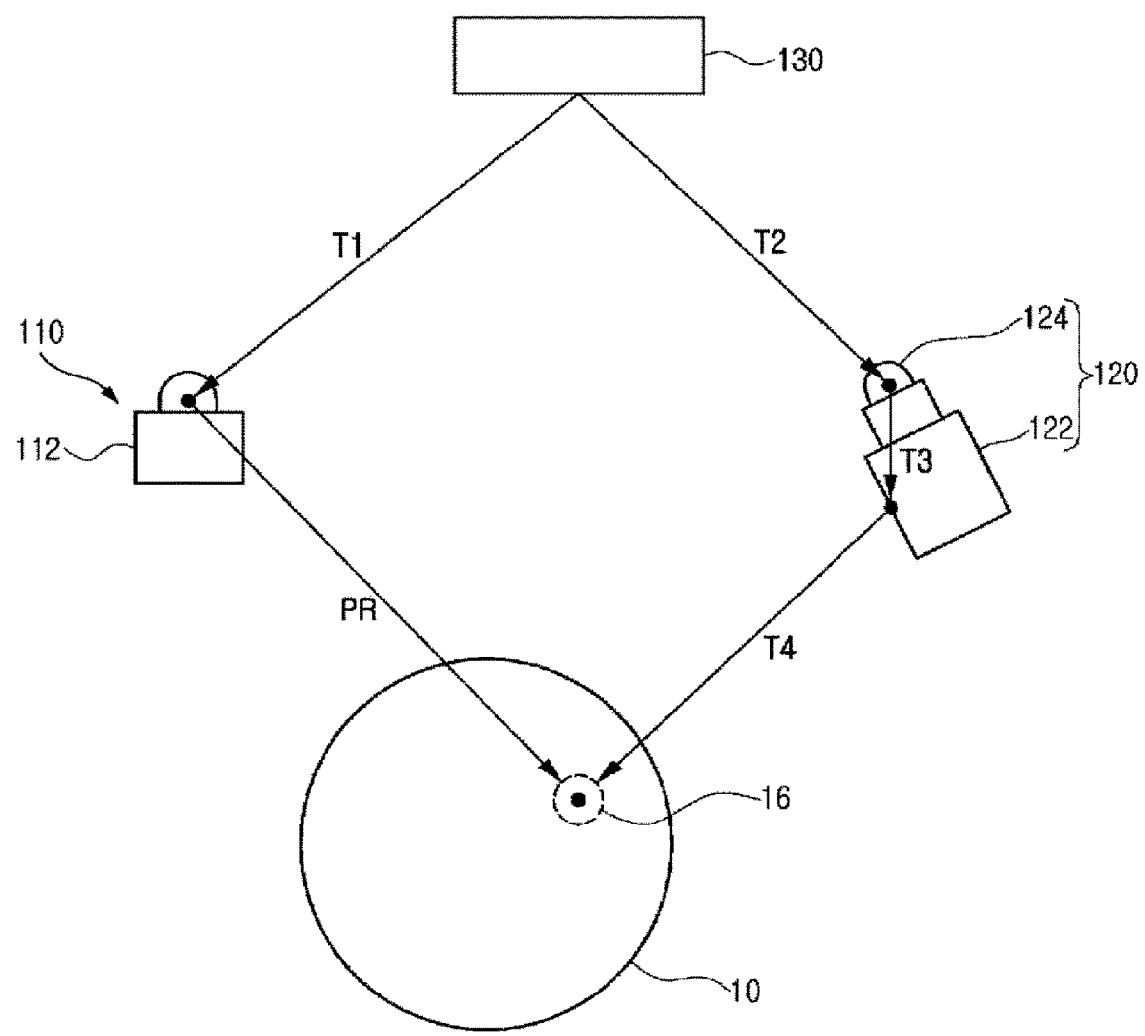
FIGS. 2 to 4 are conceptual diagrams for explaining a modeling process of the optical tracking system shown in FIG. 1.
Figure 3:
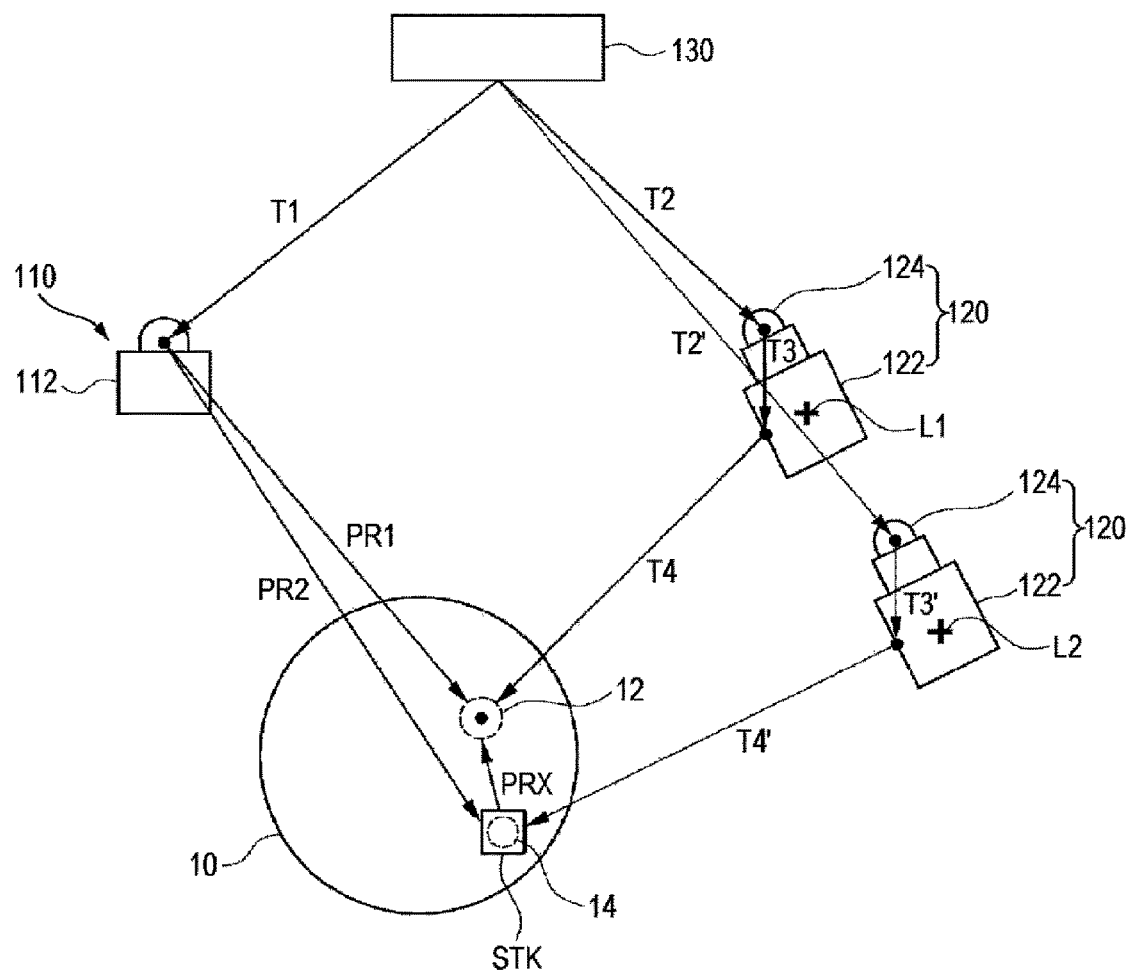
Figure 4:
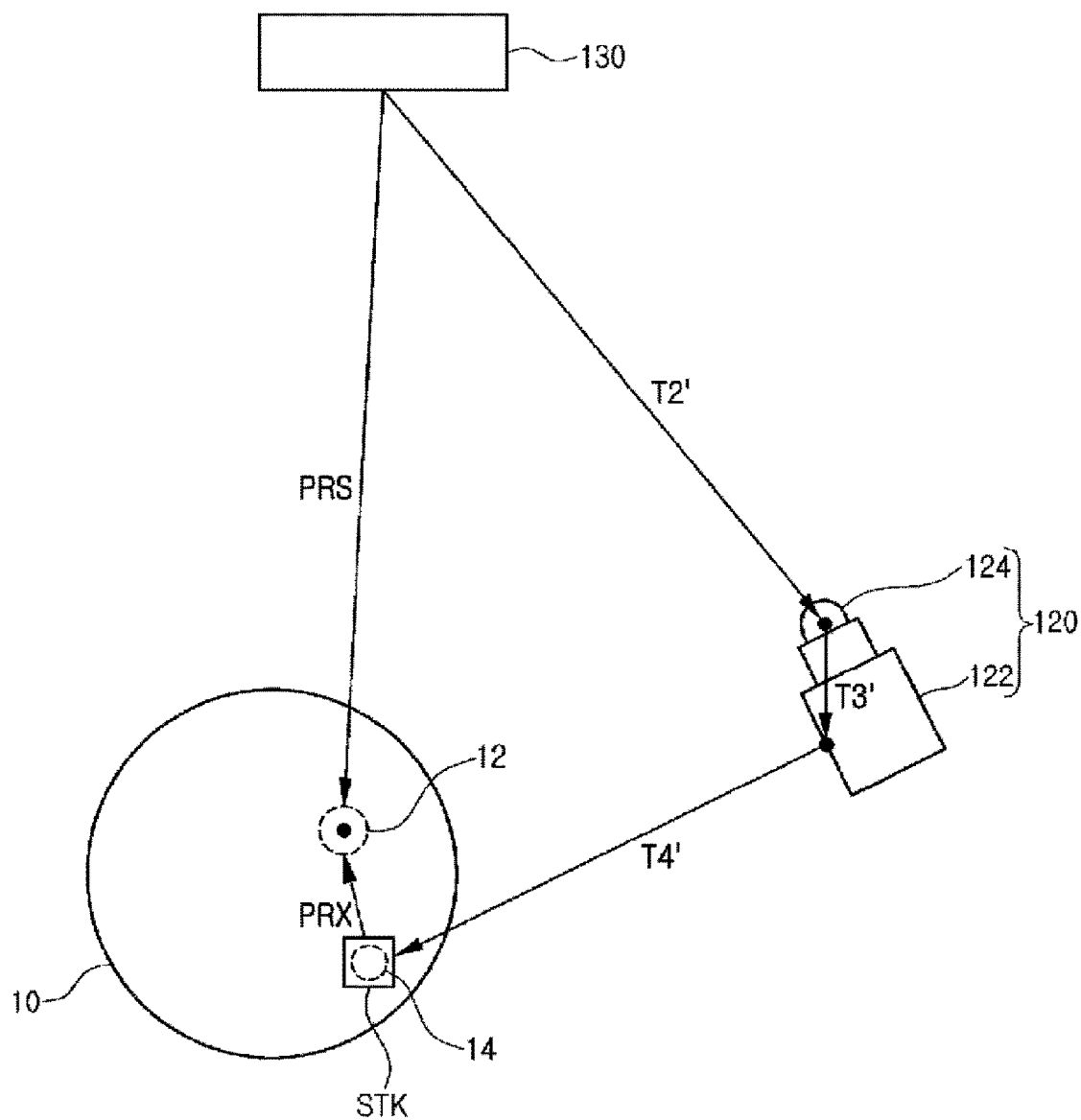

FIGS. 2 to 4 are conceptual diagrams for explaining the modeling process of the optical tracking system shown in FIG. 1.

Referring to FIG. 2, the optical tracking system 100 may represent the coordinate transformation relationships as coordinate transformation matrices T1, T2, T3, T4, and PR.

Herein, PR refers to the coordinate transformation matrix of a specified region 16 of the patient 10 with respect to the reference marker part 110. T1 refers to the coordinate transformation matrix of the reference marker part 110 with respect to the tracking sensor part 130. T2 refers to the coordinate transformation matrix of the marker 124 of the shape measurement part 120 with respect to the tracking sensor part 130. T3 refers to the coordinate transformation matrix of the measurement device 122 with respect to the marker 124 of the shape measurement part 120. T4 refers to the coordinate transformation matrix of the specified region 16 of the patient 10 with respect to the measurement device 122 of the shape measurement part 120. Herein, the specified region 16 refers to a specific region of the patient 10 including the first region 12 and the second region 14.

If the coordinate transformation matrix PR of the specified region 16 of the patient 10 with respect to the reference marker part 110 is represented by T1, T2, T3, and T4 based on the arrow directions shown in FIG. 2 so as to form a closed loop, formula 1 may be derived.

$$PR = T1^{-1}T2T3T4 \quad \text{(Formula 1)}$$

On the other hand, two different paths from the tracking sensor part 130 to the patient 10 are formed to make a closed loop, thereby deriving formula 2. Thereafter, by transforming formula 2, it is possible to derive formula 1 as the same result.

$$T1\,PR = T2T3T4 \quad \text{(Formula 2)}$$

The processing part 140 may define the coordinate system of the specified region 16 of the patient 10 relative to the reference marker part 110 by acquiring the coordinate transformation matrix PR by using formula 1 (or formula 2).

For example, the tracking sensor part 130 may measure the information for acquiring the coordinate transformation matrix T1 of the reference marker part 110 with respect to the tracking sensor part 130 and the coordinate transformation matrix T2 of the marker 124 of the shape measurement part 120 with respect to the tracking sensor part 130. The shape measurement part 120 may measure the information for acquiring the coordinate transformation matrix T4 of the specified region 16 of the patient 10 with respect to the measurement device 122 of the shape measurement part 120. The processing part 140 may acquire the coordinate transformation matrices T1, T2, and T4 by using the measured information. The processing part 140 may calculate the coordinate transformation matrix T3 of the measurement device 122 with respect to the marker 124 of the shape measurement part 120 and the coordinate transformation matrix PR of the specified region 16 of the patient 10 with respect to the reference marker part 110 from the acquired coordinate transformation matrices T1, T2, and T4.

Specifically, the coordinate transformation matrices T3 and PR may be acquired by applying the mathematical methods below. The processing part 140 may calculate the coordinate transformation matrices T3 and PR by applying such mathematical methods.

First, the coordinate transformation matrices are formed so as to include a rotational transformation part R and a positional transformation part t. Thereafter, by substituting the coordinate transformation matrices into formula 2 and arranging the same, it is possible to derive formula 3.

$$\begin{bmatrix} R_{T1} & t_{T1} \\ 0 & 1 \end{bmatrix} \begin{bmatrix} R_{PR} & t_{PR} \\ 0 & 1 \end{bmatrix} = \begin{bmatrix} R_{T2} & t_{T2} \\ 0 & 1 \end{bmatrix} \begin{bmatrix} R_{T3} & t_{T3} \\ 0 & 1 \end{bmatrix} \begin{bmatrix} R_{T4} & t_{T4} \\ 0 & 1 \end{bmatrix} \quad \text{(Formula 3)}$$

By arranging formula 3, it is possible to derive formula 4.

$$\begin{bmatrix} R_{T1}R_{PR} & R_{T1}t_{PR} + t_{T1} \\ 0 & 1 \end{bmatrix} - \begin{bmatrix} R_{T2}R_{T3}R_{T4} & R_{T2}R_{T3}t_{T4} + R_{T2}t_{T3}t_{T2} \\ 0 & 1 \end{bmatrix} = 0 \quad \text{(Formula 4)}$$

By expressing the respective components of formula 4 as an equation, formula 5 and formula 6 can be derived.

$$R_{T1}R_{PR}-R_{T2}R_{T3}R_{T4}=0 \quad \text{(Formula 5)}$$

$$R_{T1}t_{PR}+t_{T1}-R_{T2}R_{T3}t_{T4}-R_{T2}t_{T3}t_{T2}=0 \quad \text{(Formula 6)}$$

By defining $R_{TT}$ in formula 5 and arranging formula 5, formula 7 can be derived.

$$R_{TT}R_{PR}-R_{T3}R_{T4}=0, R_{TT}=R_{T2}^{-1}R_{T1} \quad \text{(Formula 7)}$$

Further, by additionally defining $t_{TT}$ in formula 6 and arranging formula 6, formula 8 can be derived.

$$R_{TT}t_{PR}-R_{T3}T4-t_{T3}=t_{TT}, t_{TT}=R_{T2}^{-1}(t_{T2}-t_{T1}) \quad \text{(Formula 8)}$$

In formulae 7 and 8, the rotational transformation matrix R has a form of 3×3 and the positional transformation matrix t has a form of 3×1. Thus, nine equations can be derived for the respective components of a 3×3 matrix from formula 7. In addition, three equations can be derived for the respective components of a 3×1 matrix from formula 8.

All the components of $R_{TT}$ (namely, all the components of $R_{T1}$ and $R_{T2}$) and all the components of $R_{T4}$ in formula 7 can be determined from the measurements described earlier. In addition, all the components of $t_{T4}$ can be determined in formula 8. Thus, there are altogether 24 unknown quantities including 9 components of each of $R_{PR}$ and $R_{T3}$ and 3 components of each of $t_{PR}$ and $t_{T4}$.

Formula 7 and formula 8 are 12 equations including 24 unknowns. Thus, it is possible to find more accurate values by performing the measurement two or more times. Accordingly, the measurement of the tracking sensor part 130 and the shape measurement part 120 may be performed two or more times.

Accordingly, the coordinate system of the specified region 16 of the patient 10 may be defined by using the coordinate transformation relationships measured as above.

The aforementioned mathematical method for acquiring the coordinate transformation matrices T3 and PR may be substituted by other methods. For example, the processing part 140 may calculate the coordinate transformation matrices T3 and PR by using a dual quaternion method.

Specifically, formula 9 below may be derived from formula 1 described above and formula 10 below may be derived by transforming formula 9.

$$T1PR-T2T3T4=0 \quad \text{(Formula 9)}$$

$$(T1+\varepsilon T1')(PR+\varepsilon PR')-(T2+\varepsilon T2')(T3+\varepsilon T3')(T4+\varepsilon T4')=0 \quad \text{(Equation 10)}$$

By developing formula 10 and eliminating a high-order term, formula 11 below can be derived.

$$T1PR'+T1'PR-T2T3T4'-T2T3'T4-T2'T3T4=0 \quad \text{(Formula 11)}$$

By transforming formula 9 and formula 11 by using a dual quaternion method, formula 12 and formula 13 below can be derived.

$$\widetilde{T1}\widetilde{PR} - \widetilde{T2T4}\widetilde{T3} = 0 \quad \text{(Formula 12)}$$

$$\widetilde{T1}'\widetilde{PR} + \widetilde{T1}\widetilde{PR}' - (\widetilde{T2T4}'' + \widetilde{T2'T4})\widetilde{T3} - \widetilde{T2T4}\widetilde{T3}' = 0 \quad \text{(Formula 13)}$$

By transforming formula 12 and formula 13 into the form of a matrix equation, formula 14 below can be derived and the coordinate transformation matrices T3 and PR may be calculated from formula 14.

$$\begin{bmatrix} \widetilde{T1} & 0 & -\widetilde{T2T4} & 0 \\ \widetilde{T1}' & \widetilde{T1} & -(\widetilde{T2T4}'' + \widetilde{T2'T4}) & -\widetilde{T2T4} \end{bmatrix} \begin{bmatrix} \widetilde{PR} \\ \widetilde{PR}' \\ \widetilde{T3} \\ \widetilde{T3}' \end{bmatrix} = 0 \quad \text{(Formula 14)}$$

Meanwhile, the processing part 140 may register the coordinate system of the three-dimensional image acquired in advance before surgically treating the patient 10 with the coordinate system of the first region 12 of the patient 10, based on the three-dimensional shape measured in the shape measurement part 120.

Specifically, instead of directly attaching a marker or a structure corresponding to the marker to the patient 10 and registering the coordinate system of the three-dimensional image with the coordinate system of the patient 10 based thereon, the coordinate system of the three-dimensional shape acquired as above (or the three-dimensional image obtained therefrom) and the coordinate system of the three-dimensional image are registered by using the three-dimensional shape itself as a marker (a natural landmark). When the specified region 16 is the first region 12, the three-dimensional shape becomes a three-dimensional shape corresponding to the lesion of the patient 10.

Referring to FIG. 3, when the specified region 16 is the first region 12, the coordinate transformation matrix of the first region 12 of the patient 10 with respect to the reference marker part 110 may be represented by PR1. Furthermore, when the specified region 16 is the second region 14, the coordinate transformation matrix of the second region 14 of the patient 10 with respect to the reference marker part 110 may be represented by PR2.

In this case, formula 1 may be represented by formula 15 in the case of the first region 12 and may be represented by formula 16 in the case of the second region 14. Formulae 2 to 14 may be modified and expressed according to formulae 15 and 16.

$$PR1=T1^{-1}T2T3T4 \quad \text{(Formula 15)}$$

$$PR2=T1^{-1}T2'T3'T4' \quad \text{(Formula 16)}$$

In this regard, PR1 and PR2 refer to coordinate transformation matrices of the first region 12 and the second region 14 of the patient 10 with respect to the reference marker part 110. Furthermore, when the positions of the shape measurement part 120 corresponding to the first region 12 and the second region 14 are assumed to be a first position L1 and a second position L2, respectively, T1 refers to a coordinate transformation matrix of the reference marker part 110 with respect to the tracking sensor part 130, T2 and T2' refer to coordinate transformation matrices of the marker 124 of the shape measurement part 120 with respect to the tracking sensor part 130 in each of the first position L1 and the second position L2, T3 and T3' refer to coordinate transformation matrices of the measurement device 122 with respect to the marker 124 of the shape measurement part 120 in each of the first position L1 and the second position L2, and T4 and T4' refer to coordinate transformation matrices of the first region 12 and the second region 14 of the patient 10 with respect to the measurement device 122 of the shape measurement part 120 in each of the first position L1 and the second position L2. Meanwhile, the first position L1 and the second position L2 merely formally indicate the positions of the shape measurement part 120 and do not specifically refer to the quantified positions.

A coordinate transformation matrix PRX of the first region 12 with respect to the second region 14 may be obtained from formulae 15 and 16 and may be represented by formula 17.

$$PRX = PR2^{-1} PR1 \quad \text{(Formula 17)}$$

Referring to FIG. 4, a coordinate transformation matrix PRS of the first region 12 with respect to the tracking sensor part 130 may be defined by formula 18 from formula 17 using the coordinate transformation matrices T2', T3' and T4' relating to the shape measurement part 120 in the second position L2 and the coordinate transformation matrix PRX. In formula 18, the coordinate transformation matrices T1, T2, T3 and T4 relating to the reference marker part 110 and the shape measurement part 120 in the first position L1 are all excluded.

$$PRS = T2'T3'T4'PRX \quad \text{(Formula 18)}$$

By applying formula 15 to formulae 2 to 14, it is possible to acquire the coordinate transformation matrices T3 and PR1. By applying formula 16 to formulae 2 to 14, it is possible to acquire the coordinate transformation matrices T3' and PR2. Therefore, the coordinate transformation matrix PRX can be acquired from formula 17. Since the second region 14 is in a rigid body registration relationship with the first region 12, the coordinate transformation matrix PRX may be regarded as a fixed immutable matrix.

Accordingly, the tracking sensor part 130 senses the shape measurement part 120, and the shape measurement part 120 measures the sticker marker part STK, whereby it is possible to continuously track the first region 12 corresponding to the lesion of the patient 10.

For example, even when the patient 10 moves or the posture changes, it is possible to apply formula 18 after the tracking sensor part 130 senses the shape measurement part 120 to acquire the coordinate transformation matrix T2' and the shape measurement part 120 measures the sticker marker part STK to acquire the coordinate transformation matrix T4'. Thus, if the method of formulae 2 to 14 is applied by assigning the coordinate transformation matrices T2', T4' and PRX to formula 18, it is possible to acquire the coordinate transformation matrices PRS and T3'. Therefore, the first region 12 of the patient 10 can be easily tracked in real time using the coordinate transformation matrix PRS.

The processing part 140 may re-register the coordinate system of the three-dimensional image acquired in advance before surgical treatment with respect to the patient 10 with the coordinate system of the first region 12 of the patient 10, based on the three-dimensional shape of the second region 14 of the patient 10 measured by the shape measurement part 120 and the third coordinate transformation relationship. In other words, the coordinate system of the second region 14 may be defined by using the three-dimensional shape of the second region 14 of the patient 10 measured by the shape measurement part 120. The first region 12 may be transformed using the coordinate transformation matrix PRX corresponding to the third coordinate transformation matrix. As a result, it is possible to re-register the coordinate system of the three-dimensional image acquired in advance before surgical treatment with respect to the patient 10 with the coordinate system of the first region 12.

The sticker marker part STK can be attached and removed with ease and may be attached to another region of the patient 10 by changing the position thereof at any time. Even in this case, it is possible to track the first region 12 of the patient 10 by re-performing the aforementioned process.

Furthermore, since the sticker marker part STK can be additionally attached with ease, an additional sticker marker part may be attached to another region of the patient 10 at any time. Even in this case, it is possible to track the first region 12 of the patient 10 by re-performing the aforementioned process.

The tracking process described above may be re-performed either automatically or manually by a user.

In one embodiment, the optical tracking system 100 may include a motion sensing part (not shown) configured to sense a motion of the patient 10. Further, instead of separately using the motion sensing part, the motion of the patient 10 may be sensed by the tracking sensor part 130. When the motion of the patient 10 is sensed by the motion sensing part or the tracking sensor part 130, the processing part 140 may re-perform the tracking process by re-performing the aforementioned process.

When the sticker marker part STK is formed so that it can be directly sensed by the tracking sensor part 130, the reference marker part 110 may be omitted by allowing the tracking sensor part 130 to directly track the sticker marker part STK. In this case, since the sticker marker part STK and the reference marker part 110 are the same, the aforementioned tracking process can be performed by defining the coordinate transformation matrices as PR1=PR2=I (unit matrix).

Hereinafter, a method of tracking a surgical instrument in the optical tracking system 100 and a process of registering the coordinate system of the surgical instrument with the coordinate system of the patient will be described in detail with reference to the drawings.

FIG. 5 is a conceptual diagram for explaining the tracking and registration of a surgical instrument in the optical tracking system shown in FIG. 1.

Referring to FIG. 5, the optical tracking system 100 may further include a surgical instrument 150.

The surgical instrument 150 is an instrument for surgically treating the patient 10 and includes a marker 152. The marker 152 is capable of radiating energy or a signal so that the energy or the signal can be sensed by the tracking sensor part 130. For example, the marker 152 may be formed in a plural number and may include pattern information.

The tracking sensor part 130 may track the surgical instrument 150 by sensing the marker 152 of the surgical instrument 150.

The processing part 140 may track the surgical instrument 150 relative to the first region 12 of the patient 10 by using a first tracking result of the surgical instrument 150 tracked by the tracking sensor part 130 and a second tracking result of the first region 12 of the patient 10 tracked relative to the tracking sensor part 130.

Specifically, a coordinate transformation relationship between the marker 152 of the surgical instrument 150 and the tracking sensor part 130 is acquired based on the first tracking result, and a coordinate transformation relationship between the first region 12 of the patient 10 and the tracking sensor part 130 is acquired based on the second tracking result. Herein, the coordinate transformation relationships may be defined, for example, in the form of a matrix and may be expressed as coordinate transformation matrices.

The processing part 140 may define a coordinate system of the surgical instrument 150 relative to the patient 10 by using the coordinate transformation relationships acquired as above. For example, the coordinate system may be defined in the form of a matrix.

That is, by using the coordinate transformation matrix PRS of the first region 12 of the patient 10 with respect to the tracking sensor part 130 and by using the coordinate transformation matrix T2" determined by sensing and calculation by the tracking sensor part 130, it is possible to determine the coordinate transformation matrix T5 of the surgical instrument 150 relatively defined with respect to the first region 12 of the patient 10 according to the following formula 19.

$$PRS = T2''T5 = T2''T3''T4'' \qquad \text{(Formula 19)}$$

Accordingly, by using the coordinate transformation relationships measured as above, the surgical instrument 150 may be tracked relative to the first region 12 of the patient 10, and the coordinate system of the surgical instrument 150 relative to the first region 12 of the patient 10 may be defined.

In FIG. 5 and formula 19, the coordinate transformation matrix T5 of the surgical instrument 150 is shown on the basis of the marker 152. However, the coordinate transformation matrix T5 may also be defined on the basis of a point to be tracked, for example, an end portion 154 of the surgical instrument 150. That is, the coordinate transformation matrix T5 may be defined by using the coordinate transformation matrix T3" of the end portion 154 of the surgical instrument 150 with respect to the marker 152 of the surgical instrument 150 and the coordinate transformation matrix T4" of the first region 12 of the patient 10 with respect to the end portion 154 of the surgical instrument 150 (T5=T3"T4"). In this case, T3" may be determined from the geometric shape of the surgical instrument 150. Thus, the coordinate system of the surgical instrument 150 relative to the patient 10 may be defined on the basis of the end portion 154.

In the meantime, the processing part 140 may register the coordinate system of the three-dimensional image acquired in advance before surgically treating the patient 10 with the coordinate system of the surgical instrument 150 relatively defined with respect to the first region 12 of the patient 10, based on the registration result of the coordinate system of the three-dimensional image and the coordinate system of the first region 12 of the patient 10.

That is, as described with reference to FIGS. 1 and 2, the coordinate system of the three-dimensional image acquired in advance before surgically treating the first region 12 of the patient 10 and the coordinate system of the first region 12 of the patient 10 may be registered based on the three-dimensional shape measured in the shape measurement part 120. As described above, the coordinate system of the surgical instrument 150 relative to the first region 12 of the patient 10 may be defined. Accordingly, the coordinate system of the three-dimensional image acquired in advance before surgically treating the first region 12 of the patient 10 and the coordinate system of the surgical instrument 150 relatively defined with respect to the first region 12 of the patient 10 may be registered with each other.

The optical tracking system 100 may further include a display part (not shown) connected to the processing part 140. The display part may display the three-dimensional image acquired in advance before surgical treatment, the image for the three-dimensional shape measured in the shape measurement part 120, an image for the surgical instrument 150, an overlapped image of the aforementioned images registered with each other, etc.

In this manner, the processing part 140 may define the coordinate system of the surgical instrument 150 relative to the first region 12 of the patient 10 from the coordinate transformation relationships and may track the surgical instrument 150 in real time during surgical treatment.

Hereinafter, a process of registering the coordinate system of the three-dimensional image captured in advance before surgical treatment with the coordinate system of the actual world during surgical treatment where the lesion of the patient and the surgical instrument are positioned, by using the optical tracking system 100, and a method of tracking the lesion of the patient and the surgical instrument will be described with reference to the drawings.

FIG. 6 is a flowchart showing a coordinate registration method and a tracking method for an optical tracking system according to one embodiment of the present disclosure.

Referring to FIGS. 2 to 6, a three-dimensional image, for example, a CT image, including the first region 12 corresponding to the lesion of the patient 10 is first acquired before surgically treating the patient 10 (S110).

The three-dimensional image such as a CT image or the like (including the reconstructed image thereof) acquired in advance before surgical treatment in the aforementioned manner may be stored in, for example, a computer.

Then, the surgical treatment procedures are performed in the following manner.

First, the reference marker part 110 stationarily disposed relative to the patient 10 and the shape measurement part 120 disposed in the first position L1 so as to measure the three-dimensional shape of the first region 12 of the patient 10 are sensed by the tracking sensor part 130 (S120).

Next, the first coordinate transformation relationship among the reference marker part 110, the tracking sensor part 130, the shape measurement part 120, and the first region 12 of the patient is acquired based on the sensing result of the tracking sensor part 130 and the measurement result of the shape measurement part 120 disposed in the first position L1 (S130).

At this time, the coordinate transformation relationship between the reference marker part 110 and the tracking sensor part 130 and the coordinate transformation relationship between the shape measurement part 120 and the tracking sensor part 130 are acquired based on the sensing result sensed in the tracking sensor part 130, and the coordinate transformation relationship between the first region 12 of the patient 10 and the shape measurement part 120 is acquired based on the measurement result of the shape measurement part 120. This makes it possible to acquire the first coordinate transformation relationship.

Then, the sticker marker part STK attached in a sticker form to the second region 14 capable of being rigidly registered with the first region 12 and the shape measurement part 120 disposed in the second position L2 so as to measure the three-dimensional shape of the second region 14 are sensed by the tracking sensor part 130 (S140).

Next, the second coordinate transformation relationship between the reference marker part 110, the tracking sensor part 130, the shape measurement part 120 and the second region 14 of the patient 10 is acquired based on the sensing result of the tracking sensor part 130 and the measurement result of the shape measurement part 120 disposed in the second position L2 (S150).

At this time, the coordinate transformation relationship between the reference marker part 110 and the tracking sensor part 130 and the coordinate transformation relationship between the shape measurement part 120 and the tracking sensor part 130 are acquired based on the sensing result sensed in the tracking sensor part 130, and the coordinate transformation relationship between the second region 14 of the patient 10 and the shape measurement part 120 is acquired based on the measurement result of the shape measurement part 120. This makes it possible to acquire the second coordinate transformation relationship.

Then, the third coordinate transformation relationship between the first region 12 and the second region 14 is extracted from the first and second coordinate transformation relationships, thereby tracking the first region 12, namely the lesion, relative to the tracking sensor part 130 (S160).

At this time, as the first region 12 is tracked, it is possible to define the coordinate system of the first region 12 relative to the tracking sensor part 130.

Meanwhile, the coordinate system of the three-dimensional image acquired before surgically treating the patient 10 and the coordinate system of the first region 12 of the patient 10 may be registered with each other based on the three-dimensional shape measured in the shape measurement part 120 (S170).

In this manner, the coordinate system of the first region 12 of the patient 10 may be relatively defined with respect to the tracking sensor part 130, and the coordinate system of the three-dimensional image such as a CT image or the like acquired in advance may be registered with the coordinate system of the first region 12 of the patient 10.

The surgical instrument 150 having the marker 152 attached thereto is provided to a surgical operator such as a doctor. The surgical operator operates the surgical instrument 150 for surgically treating the patient 10, either directly or through the use of equipment such as a surgical robot or the like. The following tracking procedures are performed with respect to the surgical instrument 150.

The tracking sensor part 130 senses the marker 152 of the surgical instrument 150 (S180).

Then, the surgical instrument 150 is tracked relative to the first region 12 of the patient 10 by using the tracking result of the tracked surgical instrument 150 and the tracking result of the first region 12 of the patient 10 relatively tracked with respect to the tracking sensor part 130 (S190).

Subsequently, the coordinate system of the three-dimensional image acquired as above and the coordinate system of surgical instrument 150 relatively defined with respect to the first region 12 of the patient 10 according to the tracking of the surgical instrument 150 are registered with each other based on the registration result of the coordinate system of the three-dimensional image and the coordinate system of the first region 12 of the patient 10 (S200).

In this manner, the coordinate system of the surgical instrument 150 for surgically treating the patient 10 is relatively defined with respect to the first region 12 of the patient 10, and the coordinate system of the three-dimensional image such as a CT image or the like acquired in advance may be registered with the coordinate system of the surgical instrument 150.

In the present embodiment, the coordinate system registration method for the optical tracking system 100 has been briefly described with reference to the flowchart of FIG. 6. However, because the specific operations of the optical tracking system 100 are substantially the same as those described earlier with reference to FIGS. 1 to 5, detailed descriptions that are duplicative will be omitted.

According to the optical tracking system and the tracking method of the present disclosure, the sticker marker part is provided in a position capable of being rigidly registered with a lesion. The shape measurement part measures three-dimensional shapes of the lesion and the sticker marker part. The tracking sensor part senses the shape measurement part and the reference marker part. The coordinate transformation relationship between the lesion and the sticker marker part is extracted from the coordinate transformation relationships between them. Thus, it is possible to track the position and posture of the lesion with respect to the tracking sensor part by merely performing a work in which the shape measurement part tracks the sticker marker part by using the coordinate transformation relationship.

Furthermore, the process in which the shape measurement part measures the sticker marker part may be re-performed with ease. Therefore, even when the patient moves or the posture changes, it is possible to easily and accurately track the lesion and the surgical instrument in real time during surgical treatment by using the coordinate transformation relationship between the lesion and the sticker marker part.

Furthermore, after surgical treatment is started, the lesion may be tracked when the shape measurement part measures the sticker marker part without having to measure the lesion. Therefore, there is no need to move the shape measurement part during surgical treatment in order to measure the lesion and it is possible to prevent a problem that the shape measurement part becomes an obstacle in surgical treatment when the shape measurement part is positioned around the lesion during the surgical treatment. Moreover, since the attachment position of the sticker marker part can be selected relatively freely, it is possible to dispose the shape measurement part in a position where the shape measurement part does not become an obstacle in surgical treatment. In addition, the sticker marker part is of a sticker attachment type. Thus, the sticker marker part may be formed in a shape that does not become an obstacle in surgical treatment, and may be attached in a position where the sticker marker part does not become an obstacle in surgical treatment. A plurality of sticker marker parts may be adopted and may be utilized in such a way as not to hinder surgical treatment.

Furthermore, when the sticker marker part is manufactured in a three-dimensional shape, it is possible to facilitate registration through the addition of feature points. If the sticker marker part is directly tracked by the tracking sensor part, it is possible to omit the reference marker part. In addition, in the case of adopting two or more sticker marker parts and two or more shape measurement parts corresponding thereto, it is possible to measure an angle by using the coordinate transformation relationship between the sticker marker parts. This makes it possible to perform surgical treatment such as knee surgery or the like through the measurement of an angle.

In addition, registration can be performed by using the three-dimensional shape of the patient measured during surgical treatment as a marker. Therefore, even though a DRB is not directly attached to the patient, the coordinate system of the three-dimensional image acquired in advance before surgical treatment can be registered with the coordinate system of the patient and the coordinate system of the surgical instrument, which may move in real time during surgical treatment. Further, even when acquiring the three-dimensional image in advance, the DRB does not need to be attached and the resetting and re-registration of the coordinate systems can be performed at any time.

Accordingly, the problems in the related art, such as the pain experienced by the patient or an error due to directly attaching the marker to the patient, the onerous work of manufacturing the STAMP before a surgery, substantial time and cost required in manufacturing the STAMP, etc., may be solved.

That is, the setting of the coordinate system of the patient and the registration of the images can be expeditiously performed in an operating room without a separate preparation process. It is therefore possible to accurately and easily perform the setting of the coordinate system of the patient and the coordinate system of the surgical instrument and the registration of the images in a shorter time and with a reduced cost. Further, it is possible to alleviate the pain of the patient and side effects by using the sticker-type sticker marker part instead of the DRB.

Thus, according to the optical tracking system according to the present disclosure and the tracking method using the same, it is possible to greatly enhance the convenience of the patient and the operator.

While the present disclosure has been described above with reference to the preferred embodiments, a person skilled in the relevant technical field or a person having ordinary knowledge in the relevant technical field will be able to diversely modify or change the present disclosure without departing from the spirit and technical scope of the present disclosure defined in the appended claims. Accordingly, it shall be construed that the foregoing descriptions and the accompanying drawings are not intended to limit the technical idea of the present disclosure but are intended to illustrate the present disclosure.

What is claimed is:

1. An optical tracking system for tracking a patient or a surgical instrument for surgically treating the patient by using a three-dimensional image for a first region corresponding to a lesion of the patient, which is acquired before surgically treating the patient, comprising:
    a reference marker disposed away from the first region of the patient and configured to radiate energy or a signal;
    a sticker marker attached in a sticker form to a second region rigidly registered with the first region;
    a measurement device configured to measure three-dimensional shapes of the first region and the second region;
    a marker installed on the measurement device and configured to radiate energy or a signal;
    a tracking sensor configured to sense the energy or the signal respectively radiated by the reference marker and the marker in order to track the reference marker and the measurement device, respectively; and
    a processor configured to acquire a first coordinate transformation relationship among the reference marker, the tracking sensor, the measurement device, the marker and the first region of the patient and a second coordinate transformation relationship among the reference marker, the tracking sensor, the measurement device, the marker and the second region of the patient based on a sensing result of the tracking sensor and a measurement result of the measurement device, and to track the first region relative to the tracking sensor by extracting a third coordinate transformation relationship between the first region and the second region from the first and second coordinate transformation relationships.

2. The optical tracking system according to claim 1, wherein when the measurement device is disposed in a first position, the processor is configured to acquire the first coordinate transformation relationship by acquiring a coordinate transformation relationship between the reference marker and the tracking sensor and a coordinate transformation relationship between the measurement device and the tracking sensor based on a sensing result of the tracking sensor, and by acquiring a coordinate transformation relationship between the first region of the patient and the measurement device based on a measurement result of the measurement device disposed in the first position, and wherein when the measurement device is disposed in a second position different from the first position, the processor is configured to acquire the second coordinate transformation relationship by acquiring a coordinate transformation relationship between the reference marker and the tracking sensor and a coordinate transformation relationship between the measurement device and the tracking sensor based on a sensing result of the tracking sensor, and by acquiring a coordinate transformation relationship between the second region of the patient and the measurement device based on a measurement result of the measurement device disposed in the second position.

3. The optical tracking system according to claim 1, wherein the processor is configured to acquire a coordinate transformation relationship between the marker and the tracking sensor and a coordinate transformation relationship between the measurement device and the marker.

4. The optical tracking system according to claim 3, wherein the coordinate transformation relationships are expressed as coordinate transformation matrices, and
    wherein the processor is configured to define the first coordinate transformation relationship and the second coordinate transformation relationship according to the following mathematical formula:

$$PR = T1^{-1} T2 T3 T4$$

where PR is a coordinate transformation matrix of the first region or the second region of the patient with respect to the reference marker, T1 is a coordinate transformation matrix of the reference marker with respect to the tracking sensor, T2 is a coordinate transformation matrix of the marker with respect to the tracking sensor, T3 is a coordinate transformation matrix of the measurement device with respect to the marker, and T4 is a coordinate transformation matrix of the first region or the second region of the patient with respect to the measurement device.

5. The optical tracking system according to claim 4, wherein the tracking sensor is configured to measure an information for acquiring the coordinate transformation matrix T1 of the reference marker with respect to the tracking sensor and the coordinate transformation matrix T2 of the marker with respect to the tracking sensor,
    wherein the measurement device is configured to measure an information for acquiring the coordinate transformation matrix T4 of the first region or the second region of the patient, and
    wherein the processor is configured to acquire the coordinate transformation matrices T1, T2, and T4 by using the measured information and to calculate, from the acquired coordinate transformation matrices T1, T2, and T4, the coordinate transformation matrix T3 of the measurement device with respect to the marker and the coordinate transformation matrix PR of the first region or the second region of the patient with respect to the reference marker.

6. The optical tracking system according to claim 5, wherein the tracking sensor and the measurement device measure two or more times with respect to each of the first region and the second region of the patient.

7. The optical tracking system according to claim 5, wherein the third coordinate transformation relationship is expressed as a coordinate transformation matrix PRX defined by the following mathematical formula:

$$PRX = PR2^{-1} PR1$$

where PR1 is a coordinate transformation matrix of the first region of the patient with respect to the reference marker, and PR2 is a coordinate transformation matrix of the second region of the patient with respect to the reference marker, and wherein the processor is configured to relatively track the first region with respect to the tracking sensor by using the coordinate transformation matrix PRX.

8. The optical tracking system according to claim 1, wherein the processor is configured to register a coordinate system of the three-dimensional image acquired before surgically treating the patient with a coordinate system of the first region of the patient based on the three-dimensional shapes measured in the measurement device.

9. The optical tracking system according to claim 8, wherein the processor is configured to re-register the coordinate system of the three-dimensional image acquired before surgically treating the patient with the coordinate system of the first region of the patient based on the three-dimensional shape of the second region of the patient measured in the measurement device and the third coordinate transformation relationship.

10. The optical tracking system according to claim 1, further comprising:
    a surgical instrument provided to surgically treat the patient, and including a marker radiating energy or a signal,
    wherein the tracking sensor is configured to sense the energy or the signal radiated by the marker of the surgical instrument so as to track the surgical instrument, and
    wherein the processor is configured to relatively track the surgical instrument with respect to the first region of the patient by using a tracking result of the surgical instrument tracked by the tracking sensor and a tracking result of the first region of the patient relatively tracked with respect to the tracking sensor.

11. The optical tracking system according to claim 1, wherein the sticker marker includes a marker having a three-dimensional shape.

12. The optical tracking system according to claim 1, wherein a plurality of sticker markers are respectively attached to different regions.

13. A tracking method for an optical tracking system, comprising:
    acquiring a three-dimensional image including a first region corresponding to a lesion of a patient before surgically treating the patient;
    sensing, by a tracking sensor, a measurement device disposed in a first position so as to measure a three-dimensional shape of a reference marker disposed away from the first region of the patient and a three-dimensional shape of the first region;
    acquiring a first coordinate transformation relationship among the reference marker, the tracking sensor, the measurement device, a marker installed on the measurement device and the first region of the patient based on a first sensing result of the tracking sensor and a measurement result of the measurement device disposed in the first position;
    sensing, by the tracking sensor, the measurement device disposed in a second position so as to measure a three-dimensional shape of a sticker marker attached in a sticker form to a second region rigidly registered with the first region and a three-dimensional shape of the second region;
    acquiring a second coordinate transformation relationship among the reference marker, the tracking sensor, the measurement device, the marker and the second region of the patient based on a second sensing result of the tracking sensor and a measurement result of the measurement device disposed in the second position; and
    tracking the first region relative to the tracking sensor by extracting a third coordinate transformation relationship between the first region and the second region from the first and second coordinate transformation relationships.

14. The tracking method according to claim 13, wherein the acquiring the first coordinate transformation relationship comprises acquiring the first coordinate transformation relationship by acquiring a coordinate transformation relationship between the reference marker and the tracking sensor and a coordinate transformation relationship between the measurement device and the tracking sensor based on the first sensing result of the tracking sensor, and by acquiring a coordinate transformation relationship between the first region of the patient and the measurement device based on the measurement result of the measurement device disposed in the first position, and
    wherein the acquiring the second coordinate transformation relationship comprises acquiring the second coordinate transformation relationship by acquiring a coordinate transformation relationship between the reference marker and the tracking sensor and a coordinate transformation relationship between the measurement device and the tracking sensor based on the second sensing result of the tracking sensor and by acquiring a coordinate transformation relationship between the second region of the patient and the measurement device based on a measurement result of the measurement device disposed in the second position.

15. The tracking method according to claim 13, further comprising:
    registering a coordinate system of the three-dimensional image acquired before surgically treating the patient with a coordinate system of the first region of the patient based on the three-dimensional shapes measured in the measurement device.

16. The tracking method according to claim 13, further comprising:
    sensing a marker of a surgical instrument so as to track the surgical instrument for surgically treating the patient; and
    relatively tracking the surgical instrument with respect to the first region of the patient by using a tracking result of the surgical instrument tracked by the tracking sensor and a tracking result of the first region of the patient relatively tracked with respect to the tracking sensor.

17. The tracking method according to claim 16, further comprising:
    after the relatively tracking the surgical instrument with respect to the first region of the patient, registering a coordinate system of the three-dimensional image with a coordinate system of the surgical instrument relatively defined with respect to the first region of the patient according to the tracking of the surgical instrument, based on a registration result of the coordinate system of the three-dimensional image and the coordinate system of the first region of the patient.

18. An optical tracking system for tracking a patient or a surgical instrument for surgically treating the patient by using a three-dimensional image for a first region corresponding to a lesion of the patient, which is acquired before surgically treating the patient and including a first region corresponding to a lesion of the patient, comprising:
- a sticker marker attached in a sticker form to a second region rigidly registered with the first region;
- a measurement device configured to measure three-dimensional shapes of the first region and the second region;
- a marker installed on the measurement device and configured to radiate energy or a signal;
- a tracking sensor configured to sense the sticker marker and the energy or the signal radiated by the marker so as to track the sticker marker and the measurement device, respectively; and
- a processor configured to acquire a coordinate transformation relationship between the sticker marker and the tracking sensor and a coordinate transformation relationship between the measurement device, the marker and the tracking sensor based on a sensing result of the tracking sensor, to acquire a coordinate transformation relationship between the first region of the patient and the measurement device based on a measurement result of the measurement device, and to relatively define a coordinate system of the first region of the patient with respect to the sticker marker by using the acquired coordinate transformation relationships.

* * * * *